United States Patent [19]

Filachek et al.

[11] Patent Number: 4,730,067

[45] Date of Patent: Mar. 8, 1988

[54] PROCESS FOR THE PREPARATION OF ZIRCONIUM CARBOXYLATE

[75] Inventors: Lawrence A. Filachek, Englishtown, N.J.; Stanley E. Whitehead, deceased, late of New Brunswick, N.J.; by James M. Whitehead, executor, Anchorage, Ak.

[73] Assignee: Akzo America Incorporated, New York, N.Y.

[21] Appl. No.: 830,975

[22] Filed: Feb. 18, 1986

[51] Int. Cl.$^4$ .......................... C07F 7/00; C11C 1/00
[52] U.S. Cl. ........................................ 556/55; 260/414
[58] Field of Search ........................... 260/414; 556/55

[56] References Cited

U.S. PATENT DOCUMENTS

| | | | |
|---|---|---|---|
| 2,221,975 | 11/1940 | Kinzie et al. | 260/414 |
| 2,252,658 | 8/1941 | Bigelow | 260/414 |
| 2,316,141 | 4/1943 | Wainer | 556/55 |
| 2,417,071 | 3/1947 | Gebhart et al. | 556/55 X |
| 2,424,262 | 7/1947 | Wainer | 556/55 |
| 2,482,816 | 9/1949 | Van Mater | 260/414 X |
| 2,498,514 | 2/1950 | Van Mater | 556/55 X |
| 2,739,905 | 3/1956 | Mack et al. | 260/414 X |
| 3,036,101 | 5/1962 | Tittle | 556/55 X |
| 3,078,288 | 2/1963 | Olson | 260/414 |

*Primary Examiner*—Helen M. S. Sneed
*Attorney, Agent, or Firm*—Francis W. Young; Louis A. Morris

[57] ABSTRACT

A process is described for the production of zirconium carboxylate comprising combining a carboxylate and a zirconium salt within a basic environment of a basic aqueous solution. The carboxylate is provided in an amount sufficient to give a ratio of carboxylate to zirconium equivalents in a range of from about 1.0:1.0 to 1.40:1.0 and the basic environment is provided by a basic salt in an amount sufficient to leave an excess of base after the combination of the zirconium salt and the carboxylate, whereupon the zirconium reacts in one step to form the zirconium carboxylate product.

15 Claims, No Drawings

PROCESS FOR THE PREPARATION OF ZIRCONIUM CARBOXYLATE

BACKGROUND

Zirconium salts of carboxylic acids are useful as dryer catalysts in substances such as paints and coatings. Zirconium carboxylate can also be used to increase the viscosity of oil and to form greases. According to "Zirconium Chemistry in Industry" *In Journal of Chemical Education* Pgs. 604–610; VOl. 39; No. 12; DEC. 1962, aqueous zirconyl and basic zirconyl chlorides react with alkali soaps to form zirconium soaps, generally containing one zirconium atom per fatty acid radical. The zirconium acylates or soaps produced are soluble in non-polar solvents, and can be used to increase the viscosity of oils and to form greases.

Several methods for preparing zirconium soaps are described in U.S. Pat. No. 3,036,101 including: (1) Reacting the sodium salt of the carboxylic acid with a water soluble inorganic zirconium salt such as zirconium oxychloride or sodium zirconium sulfate. According to this teaching the resulting water insoluble zirconium soap is extracted by solution in a suitable organic solvent and the solvent is then removed by distillation. (2) A method reacting water-insoluble zirconium carbonate, derived from a water-soluble zirconium inorganic salt and sodium carbonate is agitated with the organic acid. The resulting zirconium soap is then dissolved in the organic solvent and removed by extraction.

The disclosed invention in U.S. Pat. No. 3,036,101 calls for reacting water insoluble zirconium basic sulfate with a monocarboxylic acid in the presence of an alkali agent, said alkali agent being present in a concentration stoichoimetrically equivalent to the sulfate content of the zirconium basic sulfate. In accordance with this process the alkali agent can consist of alkali metal hydroxides, alkali metal carbonates, alkali earth metal oxides and alkali earth metal hydroxides. In a preferred embodiment this reference indicates that the organic acid is partially neutralized with the alkali equivalent to the sulfate and zirconium carboxylate is formed by the reaction of the partially neutralized organic acid with the zirconium basic sulfate.

U.S. Pat. No. 2,739,905 specifically describes the production of zirconyl 2-ethylhexanoate by the double decomposition of water soluble zirconium salt such as zirconium oxychloride or zirconium sodium sulfate with an alkali 2-ethylhexanoate, or by the fusion of insoluble zirconium carbonate with an excess of 2-ethylhexanoic acid. Unreacted 2-ethylhexanic acid is then removed.

Generally, the commercial production of zirconium carboxylate requires a stoichiometric excess of carboxylate relative to the zirconium. Typically the carboxylate to zirconium equivalency ratio is set at a minimum of 1.6:1.

The instant process has advantages over prior art methods in that the zirconium carboxylate product can be prepared in one process step in high yields and with high metal content, i.e. a very low carboxylate to zirconium mole ratio is achieved. In this regard, it has furthermore been discovered that with the excess of basic carbonate as employed by the instant process, the production of undesired and insoluble zirconium by-products is avoided.

BRIEF DESCRIPTION OF THE INVENTION

A zirconium carboxylate salt can be prepared by combining within a basic environment of a basic aqueous solution having a pH less than 13, a carboxylate and a zirconium salt susceptible of reacting with a carboxylate wherein the equivalency ratio of carboxylate to zirconium is in a range of from about 1.0:1.0 to 1.4:1.0, and wherein the basic environment is provided by a basic salt in an amount sufficient to leave an excess of basic equivalents after the carboxylate and the zirconium salt are combined. The basic salt is provided in excess relative to the acidic equivalents of the zirconium salt and the carboxylic acid, if an unneutralized carboxylic acid is used. Within the basic environment the zirconium carboxylate product is formed.

It is a primary object of the instant invention to provide a method for the preparation of zirconium carboxylate directly from the reactive zirconium salt using a low carboxylate to zirconium ratio. Other objects will become apparent as this description proceeds.

DETAILED DESCRIPTION

The zirconium salt used can be any zirconium salt that is susceptible of reaction with the carboxylate. This incudes all water soluble zirconium salts and all water insoluble zirconium salts which do react to form zirconium carboxylates. In the instant process, the zirconium reacts within the basic environment of the solution. By maintaining a basic environment for the zirconium reaction, the zirconium carboxylate can be formed in one step to give a product having a high zirconium content.

The term "basic environment" can be understood to be a basic area within the overall basic solution within which the reaction occurs. The basic environment is specified since, when the reactants are brought together and the reaction occurs within the solution, the basicity of the reaction area can be lost even though the overall solution may be considered basic. The instant process is susceptible to this, especially when using acidic zirconium salts such as zirconium acid sulfate, or when the process is conducted by adding an unneutralized carboxylic acid to the solution. Lack of the basic environment will result in unwanted and unreactive by-products such as zirconium hydroxides or polyzirconates.

The zirconium and the carboxylate can be combined by the addition of the zirconium salt to the basic solution containing carboxylate or by the addition of the carboxylate (as a salt or an acid) to the basic solution containing the zirconium. In either case the zirconium or the carboxylate could be added as a solid, although more preferably, a separate solution is prepared containing the zirconium salt or the carboxylate either as a salt or as an acid. The two solutions can then be combined in any convenient manner.

When the carboxylate is added as a carboxylic acid, or if a more acidic zirconium salt is used, then obviously a greater amount of base must be provided in order to have the excess base needed for the basic environment, since neutralization of base will occur. It is also preferred to use a greater excess of base to insure that the basic environment is maintained during the reaction.

When a larger amount of excess base is used, several advantages can be obtained. The combination of the zirconium and carboxylate can proceed more rapidly. If desired more concentrated solutions containing the zirconium and the carboxylate can be used. Using a solution highly concentrated in base, less care need be taken when the combination is being made since the basic environment is more stable and less likely to be lost.

The manner of addition selected for a particular case is thus influenced by such factors as the amounts of zirconium salt used, solution concentration, acidity of the zirconium salt, speed of addition, etc.

Any zirconium salt which will react with a carboxylate or which will dissolve in the basic reaction medium can be used. Acceptably the zirconium salt can be selected from the group consisting of: zirconium acid sulfate, zirconium tetrahalide, zirconium basic sulfate, zirconium oxyhalide, zirconium oxynitrate, and zirconium oxyacetate. Zirconium acid sulfate is preferred.

If a solid zirconium salt or carboxylate is added to the reaction, more time will be required for the reaction to go to completion. Preferably, therefore, a solution of the reactant is prepared which, in turn is added to the basic reaction solution in an appropriate manner. This solution can also contain base thus facilitating the maintenance of the critical basic environment.

Basic salts are used in the reaction solution in an excess amount relative to the acid equivalents of the zirconium salt and the carboxylic acid. This ensures a basic buffered environment for the reaction. The reaction solution is thus buffered within the basic pH range. The lack of a basic environment within any specific area of the reaction solution during the reaction typically will cause the formation of insoluble zirconate by-products resulting in hazy or opaque reaction product. While the precise amount of base required will depend upon the specific circumstances present in any particular case, an acceptable excess of basic equivalents relative to the zirconium salt is that amount which leaves from about 11 to about 30% excess equivalents of base after the carboxylate and the zirconium is combined. An acceptable minimum excess of equivalents of base over equivalents of zirconium salt is 11%. Preferably there is a minimum of 15% excess equivalents of base over the zirconium salt. A more preferred range for the amount of excess equivalents of base over the equivalents of zirconium salt is from about 18 to about 25% excess equivalents of base.

Some of the factors which will influence the amount of base needed in the reaction mixture in a particular instance, so as to maintain the basic environment where the reaction occurs, are manner (speed, type of mixing) of addition of the zirconium salt; solid or liquid state of the zirconium salt; concentration of the zirconium added; and acidity of the zirconium salt added.

There is no real limit as to the maximum amount of basic equivalents which can permissably be used as long as the pH resulting from the base is less than 13. The critical role of the excess base is to provide the basic environment needed for the process. This basic environment will also aid the reaction to go to completion.

Excess basic equivalents can be provided by any salt (hydroxides included), which, when added to water will dissolve to form a basic solution. Acceptably the base can be selected from the alkali, alkaline earth and ammonium salts. Preferred bases can be selected from the group consisting of: sodium hydroxide, potassium hydroxide, calcium hydroxide, magnesium hydroxide, ammonium hydroxide and carbonate salts. More preferred bases are the alkali, alkali earth metal and ammonium carbonates. It can be noted that the bicarbonates can also be used although more bicarbonate salt will be required to provide the necessary excess basic equivalents. Preferred carbonate salts are the alkali metal carbonates. The most preferred carbonate salts are ammonium, sodium, and potassium carbonate and bicarbonate.

When the carboxylate is provided by the addition of a carboxylate salt instead of by the addition of a carboxylic acid, whether it is to be added to the reaction solution, or formed therein, the carboxylic acid can be neutralized with any suitable base. The previously mentioned bases can be used. It is preferred to neutralize the carboxylic acid with an alkali or alkaline earth hydroxide and use a carbonate or bicarbonate to provide the excess base needed for the basic environment.

Carbonate is preferred as a base since it is a sufficiently weak base so that the pH will not get too high in spite of the amount of basic carbonate present. The pH of the reaction mixture should be between 7 and about 13. Preferrably, the highest pH allowed should be at approximately 12.5 since the highest pH values cause insoluble zirconate by-product to be formed. Preferably, the pH level is kept within a safer and narrower pH range of from about 7.5 to about 11.5

Either a carboxylic acid or a carboxylate salt and can be added to a basic solution containing zirconium. The carboxylate salt could also be in the basic solution preferably by neutralizing the carboxylic acid with an amount of base. Since the reaction is capable of high yields of the high metal content product the carboxylate and the zirconium may be used in a mole ratio of from 1:0:1.0 to 1.4:1.0, providing a relatively high zirconium and low carboxylate product. A slight excess of carboxylic acid will help the rection to be completed and still allow a high metal content in the reaction product.

The carboxylate selected can be linear, branched, saturated or unsaturated. Although any carboxylate desired can be used to prepare a zirconium carboxylate product, preferred carboxylates are monocarboxylates. Acceptably the carboxylate portion of the zirconium carboxylate contains from about 3 to about 25 carbon atoms. Preferably the carboxylate contains from about 5 to about 20 carbon atoms and the most preferred carboxylate contain from about 7 to about 15 carbon atoms. Some specific monocarboxylic acids which can be used to provide the carboxylate anion are: 2-ethylhexanoic acid; isooctanoic acid; isononanoic acid; isobutyric acid; neopentanoic acid; neooctanoic acid; neononanoic acid; neodecanoic acid; and naphthenic acid. The most preferred carboxylate is 2-ethylhexanoate (obtained from neutralizing 2-ethylhexanoic acid).

The temperature for the instant process can be maintained between 25° C. and 100° C. Preferably, the solutions are heated to a temperature in the range of from about 40° to about 98° C.; most preferably, the solutions are heated to a temperature in the range from about 50° to about 75° C. before the addition. When the process is conducted by adding a solution containing one of the reactants to the basic reaction solution either one or both of these solutions can be preheated preferably to a temperature in the range of from about 40°, to about 98° C. before combining. To ensure a complete reaction, heating of the reaction mixture can be continued for a sufficient length of time, preferably at temperatures in the range of from about 70° to about 98° C.

The length of time that the reaction should be held at elevated temperatures to complete reaction will depend upon such factors as the respective concentrations of the zirconium and carboxylate in the reaction solution. Acceptably, the reaction mixture is maintained at elevated temperatures for a minimum of about 15 minutes; and preferably for a minimum period of about 30 minutes.

The time needed may be minimized by using more concentrated solutions or higher temperatures. It should be noted, however, that when concentrated solutions are used, when the solutions are combined they should be mixed or stirred during addition and/or the addition extended over time in order to avoid combining the solution in a manner which will cause fluctuation in the basic pH environment thereby causing undesireable by-product. A greater amount of excess base will also help to avoid unwanted by-products.

The reaction product is typically a clear liquid. Advantageously, therefore, the product is filterable and easily recovered. A hazy or even an opaque product, however, can be obtained, when unreactive zirconium by-products form during the reaction. This especially will occur if the basic environment is lost in reaction areas within the solution during the reaction, such as when addition to the basic solution is too fast or if too concentrated a zirconium solution is used. If a hazy or opaque solution is obtained, such methods as centrifugation have to be used in order to separate the solid particles before the product can be filtered.

After the reaction, the basic character of the product mixture will help keep the product in suspension. In this state, the zirconium carboxylate may be used in situ. More typically, however, it would be desired that the zirconium carboxylate be separated and recovered in a more purified form for further use in applications that require an oil soluble form of active zirconium metal. The zirconium carboxylate can then be used as catalyst for paints, ink, oils and other products.

Recovery of the zirconium carboxylate product is preferably by extraction. This is accomplished by neutralizing the product mixture with an acid, extracting the zirconium carboxylate into an organic hydrocarbon solvent material; and then recovering the product from this material.

Any acid can be used to neutralize the reaction product. Acceptably, therefore, an acid can be selected from the group consisting of: sulfuric acid, nitric acid, hydrofluoric acid, and acetic acid. The acid used is preferably acetic acid or any mineral acid. Neutralization of the reaction product mixture will induce phase separation of the zirconium carboxylate thereby forming a solution of the zirconium carboxylate with the organic solvent.

Whether neutralizing is done before or after the addition of the organic solvent, neutralization will help separate the zirconium carboxylate product into an organic phase thereby separating it from the aqueous component of the reaction mixture. After this separation takes place the organic product phase can be collected for use. Preferably, before use, the organic product material is washed with water to remove all water soluble impurities. It is also permissible to remove solvent material and unwanted water by heating, distilling and/or low pressure evaporation.

The most preferred organic solvents to use for extraction are water immiscible non-polar hydrocarbons. Such hydrocarbon solvent material can be added to the mixture or to the basic solution before the reaction. Suitable nonpolar organic solvents can be selected which are either aromatic, aliphatic or mixtures thereof. Some specific organic solvents suitable for this purpose are: toluene, benzene, and aliphatic having from 6 to 30 carbon atoms such as: hexane, heptane, octane nonane, etc. Preferred organic solvents are mineral spirits or kerosene.

The organic solvent used in extraction to separate the zirconium carboxylate product can be added before neutralization or after neutralization. The organic solvent used for collection and separation (extraction) of the zirconium caroxylate product can even be added to one of the solutions being combined for the reaction.

Another preferred step which can be accomplished is to dry the zirconium carboxylate product (remove unwanted water). To accomplish this the product is preferably subjected to low pressure and heat so as to cause the water to evaporate.

Before or after extraction the zirconium carboxylate prouct can, if desired, be filtered. Preferably, however, filtration is done after extraction using suitable filtration apparatus. After extraction, the zirconium carboxylate product can also be further purified by such steps as distillation. Distillation can be used to remove the solvent material from the separated phase.

The best mode contemplated for the instant process is a batch reaction system, although a continuous system can also be used.

The following examples are given to illustrate the instant invention, and not to limit it. All parts and percentages are by weight unless otherwise specified.

Examples 1-3 demonstrate the excellent results obtainable by use of the instant process.

EXAMPLE 1

An aqueous solution (solution A) of zirconium acid sulfate—$ZrO(SO_4H)_2$ was prepared by adding 373.0 grams (g) of the $ZrO(SO_4H)_2$ to 460 g of water.

A second aqueous solution (Solution B) containing an excess amount of base and the desired carboxylate was prepared in the following manner: the salt of the desired carboxylate (2-ethylhexanoate) was formed in solution by combining 179.8 g of 2-ethylhexanoic acid; 800.0 g of water; and the neutralizing equivalent of 50% NaOH (99.4 g). The basic environment needed for the reaction was provided by the addition of a 209.1 g amount of 89.2% pure $Na_2CO_3$ to complete Solution B. This gave Solution B a 19.2 percent (%) excess amount of basic equivalents relative to the acidic equivalents of the zirconium salt, (an excess of 0.192 basic equivalents). These basic equivalents were in addition to the amount of carbonate which would be neutralized by the acidic sulfate of Solution A.

Solution B was preheated to 50° C., and Solution A was added to it with stirring, forming a viscous mixture which was then heated at 90°-95° C. for ½ hour to ensure a complete reaction.

The following procedure was used to collect the product:

A neutralizing amount of 72.2 g of acetic acid was added, mineral spirits in the amount 203.3 g were added as an organic solvent, stirring was halted, phase formation finished, and the organic phase, containing the zirconium 2-ethylhexanoate product was separated. This product, a clear liquid, was then dehydrated by heating it at 150° C.; and was filtered. An amount of 470.0 g of zirconium 2-ethylhexanoate was collected for a 97.9% yield. Metal content was 18% by wt.

EXAMPLE 2

Zirconium acid sulfate in an amount of 373.0 g was combined with 460 g of water to form solution A.

A second aqueous solution (Solution B) containing an excess amount of basic equivalents and the desired carboxylate was prepared in the following manner: the salt of the desired carboxylate (2-ethylhexanoate) was formed in the solution by combining 179.8 g of 2-ethylhexanoic acid, 800.0 g of water, and the neutralizing equivalent of 50% sodium hydroxide (99.9 g). A 209.1 g amount of 89.2% pure $Na_2CO_3$ was added to complete solution B to provide the basic equivalent. Solution B thus contained an excess of 0.193 basic equivalents (an excess of about 19.3% relative to the acidic sulfate of the zirconium in Solution A).

Solution B was preheated to 60° C., and with stirring, Solution A (at ambient temperatures) was added to Solution B thereby forming a viscous mixture which was stirred and heated at 90°–95° C. for ½ hour to insure a complete reaction. An amount of 55.5 g of acetic acid was added to neutralize the product mixture; mineral spirits and butyl carbitol were added for product extraction. Stirring was halted and the organic product phase was separated. The product appeared as a clear liquid. This clear liquid product was then filtered. Some product was lost due to spillage but the product not lost was approximately 22% by wt. metal and was 87.9% of the theoretical yield of zirconium 2-ethylhexanoate.

EXAMPLE 3

A reaction solution was prepared by the addition of 373.0 g of zirconium acid sulfate, 140.0 g $Na_2CO_3$, and 460 g of water. A second aqueous solution was prepared by combining 800 g of water and 283.5 g of $Na_2CO_3$. The zirconium solution was then added to the second aqueous solution. There was a combined excess in this solution of 0.784 basic equivalents of carbonate relative to the zirconium acid sulfate in addition to those amounts of carbonate neutralized by the acidic sulfate (a 78.4% excess). The basic mixture was stirred, and an amount of 179.8 g of 2-ethylhexanoic acid was then added. As stirring continued 203.3 g of mineral spirits were added as an organic phase to collect the product. The mixture was heated and held at temperatures between 90°–95° C. for ½ hour to insure a complete reaction. Acetic acid was added to the mixture to neutralize the excess carbonate. Stirring was stopped, phase formation occurred and the clear liquid organic phase containing the product was removed. The product was dehydrated and filtered. Zirconium 2-ethylhexanoate was collected in an amount of 95.5% of total possible yield (503.1 g); the metal content value was approximately 17.29%.

Examples 4–6 are offered to illustrate the results of not having the necessary basic environment in the reaction mixture during the reaction.

EXAMPLE 4

Solution A was prepared by the combination of 373.0 g of Zirconium Acid Sulfate and 460 g of water. Solution B was prepared by the combination of 800 g of water, 179.8 g of 2-ethylhexanoic acid, and 99.6 g of (a neutralizing amount) of 50% sodium hydroxide. Sodium carbonate (89.2% pure) was added to Solution B in an amount of 166.8 g to give Solution B a 0.015 excess amount of basic equivalents relative to the zirconium acid sulfate.

Solution B was preheated to 50° C. and Solution A was charged in the same manner as was used for Example 1; the mixture was heated for ½ hour at temperatures of 90°–95° C. To collect the product, 203.3 g of mineral spirits were added stirring was halted and phase formation was completed. The water phase was removed and the organic product phase was collected and dehydrated. The product was extremely milky and was not filterable.

EXAMPLE 5

Solution A was prepared by the addition of 300 g of zirconium acid sulfate to 370 g of water. A second aqueous solution (Solution B) containing an excess amount of base in an amount of 0.101 excess equivalents per equivalent of the zirconium acid sulfate of Solution A was prepared as follows: Sodium 2-ethylhexanoate was prepared in situ by adding 133.0 g of 2-ethylhexanoate acid to 643.4 g of water and a neutralizing amount of 73.9 g of sodium hydroxide (an exact equivalent). Sodium carbonate was added in an amount of 155.4 g to provide a 10.1% excess of basic equivalents per equivalent of zirconium acid sulfate. An amount of 373.7 g of mineral spirits and 15.3 g of butyl cabitol was added to provide organic phase material for product collection before combining the solutions.

Solution A was preheated to 90° C. and was then added to Solution B. The temperature of the combined solution was 83° C. The mixture was heated to 98° C. for ½ hour.

Water was removed and 900 g of fresh water was added and the mixture was heated to 90° C., and 19.8 g of acetic acid was added for neutralization. The product phase was removed and dehydrated. Product was milky white and filtration was not possible.

EXAMPLE 6

Solution A was prepared by the addition of 373 g of zirconium acid sulfate to 460 g of water.

Solution B was prepared by first forming the salt of the desired carboxylate (2-ethylhexanoate) in situ by combining 179.8 g of 2-ethylhexanoic acid and a neutralizing amount (99.9 g) of 50% sodium hydroxide in 800 g of water. $Na_2CO_3$ which was 89.2% pure was added to the Solution B in an amount of 178.9 g, thereby providing the basic environment thus an excess of basic equivalents in an amount of 10.4% excess equivalents of base per equivalent of the zirconium acid sulfate contained in Solution A was provided (in excess of the acidic sulfate).

Organic solvent material for the collection of the reaction product in an organic phase, was provided by adding mineral spirits and butyl carbitol to Solution B. Solution A was then preheated to 40° C. and charged to Solution B. After charging, this mixture was heated for ½ hour at 90°–95° C. to ensure that the reaction had gone to completion. The organic product phase was separated, and water was removed from it. The organic product was then contacted with another 1000 ml of water. This mixture was stirred, phases were allowed to form and the organic product phase separated from the aqueous phase. Water was again stripped from the product mixture. Although the product was not as milky as the product of Example 5, the product liquid appeared extremely hazy and the mixture would not filter.

DISCUSSION OF THE EXAMPLES

Examples 4 through 6 demonstrate that the basic environment is needed in the reaction medium to prevent unwanted by-products. Although Solution B of these examples was basic overall, the basic environment was lost as the combination of the solutions proceeded (use of an acidic zirconium sulfate makes such loss more likely). Thus Examples 4–6 show that a considerable amount of undesired by-product was formed due to the lack of the necessary basic environment for the reaction. This could have been avoided by adding more base or by slowing the addition of Solution A in Examples 5 or 6. When the amount of excess base is small, more care should be taken to ensure that the zirconium and the carboxylate are combined in a basic environment or area within the basic solution. When the basic solution contains a very slight excess of base this is more difficult since localized pH fluctuations will occur.

Comparing Examples 1, 5 and 6 demonstrates that for the particular concentration of the zirconium solution used and for the particular manner of adding Solution A to Solution B, the amount of excess equivalence of base per equivalence or zirconium salt which was required was probably a minimum of about 11–11.5% excess. As larger amounts of base are used, more concentrated zirconium solutions and more rapid additions of larger amounts of solution could be employed without the production of the undesired unreactive zirconium by-products. Example 4, it should be noted, shows the instant process wherein the basic carbonate equivalence was only a slight excess. As a result the basic environment within the basic solution was not well maintained during the zirconium reaction and this resulted in undesired insoluble zirconium by-products. The product was not filterable, production of zirconium carboxylate was deterred, and recovery of any zirconium carboxylate product would have required a different and probably impractical recovery method.

We claim:

1. A process for the production of zirconium carboxylate comprising: combining within a basic environment of a basic aqueous solution having a pH less than 13, a zirconium salt and a carboxylate in an amount sufficient to give a mole ratio of carboxylate to zirconium in the range of from 1:1 to about 1.4:1, said basic environment being provided by a basic salt in an amount sufficient to leave a minimum excess of about 0.11 equivalents of base relative to said zirconium salt after the combination of the zirconium salt and the carboxylate, whereupon sad zirconium salt reacts with said carboxylate within the basic environment to form zirconium carboxylate.

2. A process as described in claim 1 wherein said zirconium salt is selected from the group consisting of zirconium acid sulfate, zirconium basic sulfate, zirconium tetrahalide, zirconium oxyhalide, zirconium oxynitrate, and zirconium oxyacetate.

3. A process as described in claim 1 wherein said carboxylate is from a carboxylic acid selected from the group consisting of: isooctanoic acid; isonanoic acid; isobutyric acid; neopentanoic acid; neooctanoic acid; neonanoic acid; neodecanoic acid; naphthenic acid, and 2-ethylhexanoic acid.

4. A process as described in claim 1 wherein said basic salt comprises a carbonate salt selected from the group consisting of: ammonium carbonate, an alkaline earth metal carbonate salt, and an alkali metal carbonate salt.

5. A process as described in claim 1 wherein said zirconium salt is present in an aqueous solution which is then added to said basic aqueous solution containing a carboxylate salt.

6. A process as described in claim 5 wherein said carboxylate salt is formed in solution by neutralization of a carboxylic acid in an aqueous mixture, followed by the addition of a base to form said basic aqueous solution.

7. A process as described in claim 1 wherein said carboxylate is provided by adding a carboxylic acid to said basic aqueous solution containing said zirconium.

8. A process as described in claim 1 wherein said basic salt is present in a sufficient amount to leave, after said zirconium salt and said carboxylate are combined, 0.11 equivalents of base relative to the zirconium salt.

9. A process as described in claim 1 wherein after said zirconium and the carboxylate are combined the mixture is heated at a temperature in the range from about 40° to about 98° C. for minimum of 15 minutes, after which time the mixture is neutralized.

10. A process as described in claim 1 wherein after the reaction, the solution is neutralized, and the zirconium carboxylate is collected by extracting it with a hydrocarbon solvent.

11. A process as described in claim 10 wherein the hydrocarbon solvent is an aromatic or aliphatic hydrocarbon, or mixtures thereof.

12. A process as described in claim 5 wherein said zirconium salt is zirconium acid sulfate, said carboxylate is from 2-ethylhexanoic acid and the base is a carbonate salt.

13. A process as described in claim 7 wherein said carboxylic acid is selected from the group consisting of: isooctanoic acid; isononanoic acid; isobutyric acid; neopentanoic acid; neooctanoic acid; neonoanoic acid; neodecanoic acid; naphthenic acid, and 2-ethylhexanoic acid.

14. A process as described in claim 13 wherein said basic salt is a carbonate salt and said zirconium salt is zirconium acid sulfate.

15. A process as described in claim 5 wherein the temperature of said basic aqueous solution is in the range of from about 40° C. to about 98° C. for a minimum of about 15 minutes following addition of the zirconium salt solution, and wherein, after the zirconium carboxylate forms, said basic solution is neutralized with an acid and the zirconium carboxylate is collected by extracting it with a hydrocarbon solvent.

* * * * *